United States Patent [19]

Tallman

[11] Patent Number: 5,508,189
[45] Date of Patent: Apr. 16, 1996

[54] REGENERATION OF PLANTS FROM CULTURED GUARD CELL PROTOPLASTS

[75] Inventor: John G. Tallman, Malibu, Calif.

[73] Assignee: Pepperdine University, Malibu, Calif.

[21] Appl. No.: 233,512

[22] Filed: Apr. 26, 1994

[51] Int. Cl.⁶ .................. C12N 5/00; C12N 5/02; C12N 5/04
[52] U.S. Cl. .................. 435/240.5; 435/240.4; 435/240.47; 435/240.48; 435/240.49
[58] Field of Search .................. 435/240.4, 240.47, 435/240.48, 240.49, 240.5

[56] References Cited

U.S. PATENT DOCUMENTS

| | | | |
|---|---|---|---|
| 3,832,801 | 9/1974 | Carlson et al. | 47/58 |
| 4,003,156 | 1/1977 | Sibi et al. | 47/58 |
| 4,300,310 | 11/1981 | Galbraith | 47/58 |
| 4,418,149 | 11/1983 | Ptashne et al. | 435/253 |
| 4,499,687 | 2/1985 | Lawrence, Jr. et al. | 47/58 |
| 4,536,475 | 8/1985 | Anderson | 435/172.3 |
| 4,634,674 | 1/1987 | Shahin | 435/240 |
| 4,672,035 | 6/1987 | Davidonis et al. | 435/240.4 |
| 4,771,002 | 9/1988 | Gelvin | 435/172.3 |
| 5,041,382 | 8/1991 | Gupta et al. | 435/240.45 |
| 5,049,500 | 9/1991 | Arnizen et al. | 435/172.3 |
| 5,102,796 | 4/1992 | Hall et al. | 435/172.3 |
| 5,171,683 | 12/1992 | Kertz | 435/240.4 |

OTHER PUBLICATIONS

Zeiger 1983 Annual Rev. Plant Physiol 34:441–475.
Mansfield 1986 In Pl. Phys.: A Treatise (Sutcliffe et al ed.) Academic Press vol. 9: 155–224.
Raschke et al 1988 Botanica Acta 101: 283–294.
Tallman 1992 Critical Reviews in Pl. Science 11: 35–57.
Sack 1987 In Stomatal Function (Zeiger et al ed.) Stanford Press pp. 59–89.
Allaway et al 1972 Canadian J. Botany 50: 1405–1413.
Srivastava et al 1972 J Ultrastructure Research 39: 345–363.
Galatis et al 1980 American J Botany 67: 1243–1261.
Outlaw et al 1979 Pl. Physiol 64: 79–82.
Zeiger et al 1977 Science 196: 887–889.
Cowan et al 1982 Aust J Pl. Physiol 9: 489–498.
DeSilva et al 1985 New Phytologist 100: 473–482.
Morison 1987 In Stomatal Function (Zeiger et al ed.) Stanford Press pp. 229–251.
Zeiger et al 1982 Science 218: 680–682.
Gotow et al 1982 Plant & Cell Physol 23: 1063–1070.
Kruse et al 1989 Pl. Physiol 90: 1382–1386.
Shimazaki et al 1982 Pl and Cell Physiol 23: 871–879.
Gotow et al 1984 Pl and Cell Physiol 25: 671–675.
Cupples et al 1991 Plant, Cell and Environment 14: 691–697.
Shepard et al 1975 Pl. Physiol. 55: 689–694.
Widholm 1972 Stain Technology 47: 189–194.
Herscovich et al 1991 Pl. Science 81: 237–244.
Murashigi et al 1962 Physiologia Plantarum 15: 473–497.
Shimazaki et al 1987 Pl. Physiol. 84: 7–9.
Shimazaki et al 1989 Pl. Physiol 90: 1057–1064.
Shimizaki 1989 Pl Physiol 91: 459–463.
Dodge et al 1992 Physiologia Plantarum 86: 221–230.
Hocking 1980 Annals of Botany 45: 633–643.
Bingham 1968 Crop Sci 8: 509–510.
Sahgal et al 1994 plant Science 97: 199–208.

*Primary Examiner*—Patricia R. Moody
*Attorney, Agent, or Firm*—Cislo & Thomas

[57] ABSTRACT

Guard cell isolation and culture to regenerate the parent plant. Guard cells are collected from leaves of a plant and isolated to yield a dense and pure guard cell protoplast suspension. Cultures derived from the suspension may be grown on callus medium with excellent results. Root and shoot propagation may be obtained from established guard cell callus. With the establishment of roots and shoots, an entire plant may be regenerated from its guard cells. Guard cells may also be cultured for transplant gene extraction as a gene donor used to alter the characteristics of the recipient plant.

26 Claims, 6 Drawing Sheets

Fig. 8.
Fig. 10.
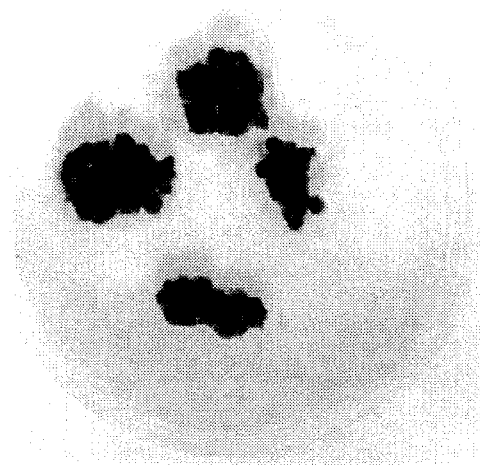
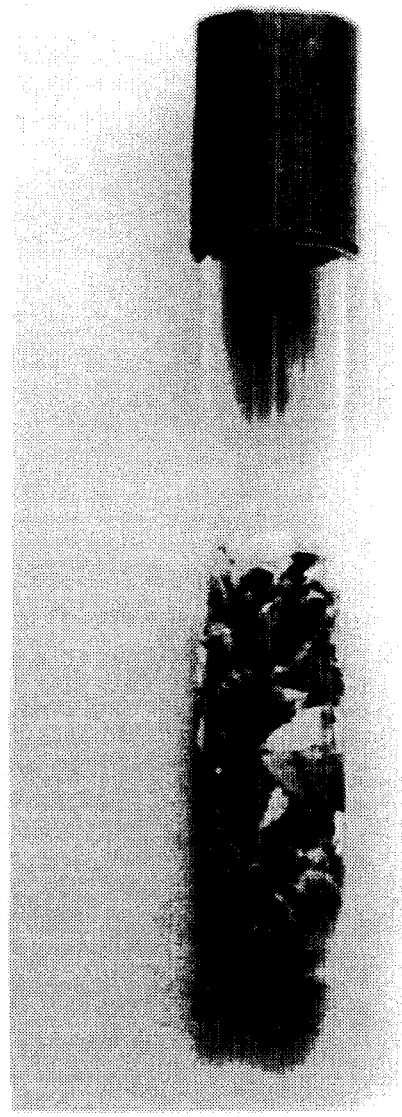
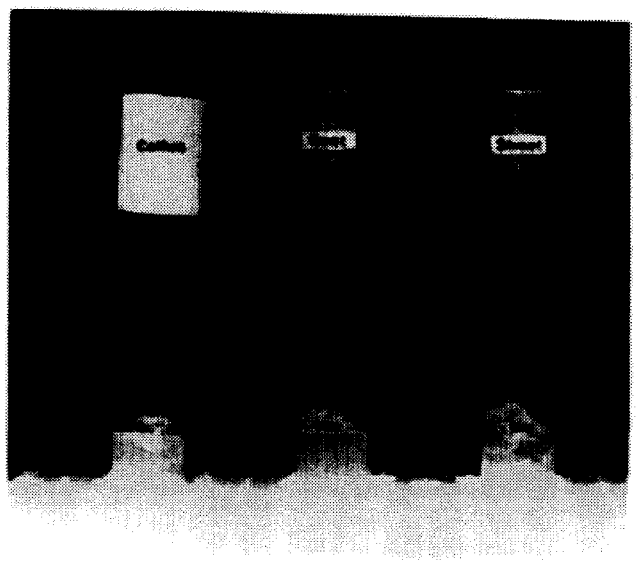
Fig. 9.

FIG. 12a.

| Constituent | Modified Medium 2 mg/l | Modified Medium 1 mg/l | Tobacco Shoot Medium mg/l | Root Medium mg/l |
|---|---|---|---|---|
| $Ca(NO_3)_2 \cdot 4H_2O$ | 180.0 | | | |
| $NH_4NO_3$ | 82.5 | 825.0 | 1650.0 | 412.5 |
| $KNO_3$ | 167.0 | 950.0 | 1900.0 | 475.0 |
| $CaCl_2 \cdot 2H_2O$ | 84.7 | 220.0 | | 110.0 |
| $CaCl_2$ | | | 333.0 | |
| $MgSO_4 \cdot 7H_2O$ | 447.3 | 1223.0 | | 611.5 |
| $MgSO_4$ | | | 181.0 | |
| $Na_2SO_4$ | 180.0 | | | |
| $KH_2PO_4$ | 68.0 | 680.0 | 170.0 | 340.0 |
| $NaH_2PO_4 \cdot H_2O$ | 14.9 | | | |
| KCl | 88.3 | | | |
| $Na_2$ EDTA | 3.7 | 37.3 | | 18.7 |
| $FeSO_4 \cdot 7H_2O$ | 2.8 | 27.8 | | 13.9 |
| $Fe_2(SO_4)_3$ | 2.3 | | | |
| KI | 0.76 | 0.83 | 0.83 | 0.42 |
| $H_3BO_3$ | 2.0 | 6.2 | 6.2 | 3.1 |
| $MnCl_4 \cdot H_2O$ | 3.1 | | 16.9 | |
| $MnCl_2 \cdot 4H_2O$ | 2.0 | 19.8 | | 9.9 |
| $ZnSO_4 \cdot 7H_2O$ | 2.3 | 9.2 | 8.6 | 4.6 |
| $Na_2MoO_4 \cdot 2H_2O$ | 0.03 | 0.25 | 0.25 | 0.13 |
| $CuSO_4 \cdot 7H_2O$ | 0.003 | 0.025 | 0.025 | 0.013 |
| $CoSO_4 \cdot 5H_2O$ | 0.003 | 0.03 | | 0.015 |
| $CoCl_2 \cdot 6H_2O$ | | | 0.025 | |
| FeNa EDTA | | | 36.7 | |

FIG. 12b.

| Constituent | Modified Medium 2 mg/l | Modified Medium 1 mg/l | Tobacco Shoot Medium mg/l | Root Medium mg/l |
|---|---|---|---|---|
| i-Inositol | 39.7 | 100.0 | 100.0 | 50.0 |
| Thiamine HCl | 0.19 | 1.0 | 0.4 | |
| Glycine | 1.35 | | 2.0 | 0.5 |
| Niacin | 0.45 | | | |
| Pyridoxine·HCl | 0.1 | | 0.5 | |
| Nicotinic acid | | | 0.5 | |
| Casein Hydrolys. | | | 1000.0 | |
| Kinetine | | | 1.0 | |
| 1-NAA | 0.3 | 0.3 | | |
| 6-Bap | 0.075 | 0.075 | | |
| Sucrose | 0.28M | 0.23M | | |
| MES | 5.0nM | 5.0nM | 0.025M | |
| Agarose | | 0.5% (w/v) | | |
| Phytagar | | | | 0.6% (w/v) |

REGENERATION OF PLANTS FROM CULTURED GUARD CELL PROTOPLASTS

STATEMENT AS TO RIGHTS TO INVENTIONS MADE UNDER FEDERALLY-SPONSORED RESEARCH AND DEVELOPMENT

The invention set forth herein was supported in part by National Science Foundation Grant MCB 9004331. The Government has certain rights in this invention.

BACKGROUND OF THE INVENTION

1. Field of the Invention

This invention relates to the regeneration of plants from excised cells, and, more particularly, to the regeneration of tobacco plants from recovered and cultured guard cells.

2. Description of the Related Art

It is possible to initiate the growth of an individual plant without the use of seeds. Such asexual reproduction may be accomplished a number of different ways. Once such way is to isolate certain types of cells from a plant, culture those cells to establish a stable population, and then promote shoot and root growth from the population to form an immature plant that can be planted in soil and grown just like a regular, seed-derived plant.

Not all types of cells in a plant can be motivated to form a new plant. Those which can are often designated as totipotent or capable of developing into a complete embryo or plant. Those which cannot are considered to be terminally differentiated and lack the ability to develop into a plant, thereby regenerating its parent. Specialized plant cells performing particular and unique functions are generally considered to be terminally differentiated. In developing their special nature, such cells may lose their totipotency.

Plant regeneration is known in the art and was achieved by Shahin (U.S. Pat. No. 4,634,674 issued Jan. 6, 1987) and Carlson, et al. (U.S. Pat. No. 3,832,801 issued Sep. 3, 1974).

In the Shahin patent, plants are regenerated from protoplasts isolated from the shoot or stem portion of pre-conditioned tomato seedlings. Shoots from germinated tomato seeds are separated from the rest of the young plant and grown in a substantially hormone free growth medium to form protoplast-donating plants. Such stems of immature plants lack any significant number of functional guard cells and do not yield guard cell protoplasts.

The Carlson, et al. patent fused mesophyll protoplasts from two Nicotiana species: *Nicotiana glauca* and *Nicotiana sylvestris* to form polyploidal hybrid cells. In performing this parasexual hybridization, Carlson, et al. used the mesophyll cells of plant leaves and discarded the epidermal layers with their guard cells.

Previously, it has been very difficult to obtain viable guard cell protoplast populations as such cells were not amenable to previously-known methods for rearing protoplasts. Often, such guard cell protoplasts would live for a limited time perhaps dividing once or twice before ceasing reproduction.

The guard cells that surround stomatal pores are specialized to transduce environmental signals into the turgor-driven cell movements that regulate plant gas exchange with the environment. Guard cells possess unique anatomical, physiological, and developmental features that reflect their function and underlie their movements. They are relatively small, have a few starch-containing chloroplasts, contain relatively high numbers of mitochondria, and have thickened, asymmetric cell walls. Unlike mesophyll cells, guard cells accumulate starch in their chloroplasts in darkness and catabolize starch in light. Guard cells extrude protons, accumulate potassium ions, and develop turgor in response to low fluences of blue light. They lose turgor when treated with abscisic acid or when subjected to high concentrations of carbon dioxide. The chloroplasts of guard cells fail to senesce (turn yellow) at the same time as chloroplasts in cells of senescing mesophyll tissue of the same leaf.

Good methods are available for preparing guard cell protoplasts free of contaminating mesophyll and epidermal cells. Such highly purified preparations containing a single cell type might be expected to exhibit homogeneous responses to cell culture protocols. Potentially, cultured guard cell protoplasts could be used to study; 1) plant cell responses to light quality and quantity; 2) cellular responses to growth regulators such as abscisic acid; 3) patterns of plant cell development, including differentiation and/or red-ifferentiation in culture; and 4) chloroplast senescence.

For these reasons, initiation was made of the systematic development of a method for culturing guard cell protoplasts of *Nicotiana glauca* (Graham), tree tobacco. This species was chosen because its leaf epidermis is easily detached, because it has large leaves with high densities of stomata, and because the genus Nicotiana is amenable to culture.

The highly specialized nature of guard cells led to examination initially as to whether they were terminally differentiated. To do so, attempts were made to establish guard cell protoplasts isolated from leaves of *N. glauca* in culture and to induce their division with plant growth regulators. The results of that study indicated that guard cells were not terminally differentiated and that they could be made to grow, synthesize cell walls, and divide in media similar to those used for culturing mesophyll cell protoplasts of other Nicotiana species.

The experiments leading to the present invention were undertaken for two reasons. First, the results of previous experiments suggested that optimal conditions for culturing guard cells had not been achieved. The percentage of cells surviving 96 h in culture, the time at which the first cell divisions began, was less than ten percent (<10%) of the original number of cells used to initiate the culture. By day 7 of culture, survival had declined to less than one percent (<1%) of the original number of cells. Although 80% of the cells surviving 7 days in culture divided, concerns arose about using callus derived from such a small number of original guard cell protoplasts to regenerate plants, since it could be argued that the surviving cells were a small subpopulation of protoplasts that were not representative of the cells of the initial isolate.

Although no morphological evidence to that effect was found, the possibility that the dividing cells might be a subpopulation that was more responsive to the peculiar culture conditions employed or that they were those guard cells most recently differentiated from progenitor cells could not be ruled out. Thus, determination was sought as to whether adjustments to culture conditions could increase the percentage of guard cell protoplasts surviving in culture.

Second, a demonstration of totipotency is usually viewed as an important step in the development of a culture protocol for a cell type which has never before been cultured. Such a demonstration is necessary to ensure that the culture conditions employed do not alter the genome to such an extent that plants cannot be recovered from callus derived from the cultured cells. Because no demonstration of totipotency has been made for cultured guard cells of any species, the hypothesis was tested that cultured guard cell protoplasts of *Nicotiana glauca* are totipotent by attempting to regenerate plants from callus derived from cultured guard cell protoplasts.

SUMMARY OF THE INVENTION

The present invention dwells upon the regeneration of plants by the culturing and activation of guard cells. Guard cells are collected from plant leaves and treated to eliminate all other plant cells and materials. The cell walls of the guard cells are then removed to yield guard cell protoplasts in a very high and pure concentration. Guard cell protoplasts are then grown in different media to first establish the guard cell population and then augment the guard cell population. Shoot and root growth are then promoted in the guard cell populations to form an immature plant which can then be planted in soil and behaves and grows like the original parent plant.

Experiments were performed to optimize conditions for culturing guard cell protoplasts of *Nicotiana glauca* and to determine whether cultured guard cell protoplasts were totipotent. Guard cell protoplasts were isolated from adaxial epidermal tissue of leaves of *Nicotiana glauca* grown under fluorescent light (800–900 $\mu$mol $m^{-2}$ $s^{-1}$ of photons of photosynthetically active radiation).

To increase the probability that guard cells were of uniform osmotic potential at the time leaves were harvested, leaves were collected in darkness, just before the beginning of each light period. Protoplasts were cultured in liquid media similar to those used for culturing mesophyll cell protoplasts of *Nicotiana tabacum*, but of modified pH and KCl, $CaCl_2$, sucrose, and glycine concentrations. Concentrations of growth regulators were 0.3 mg $l^{-1}$ $\alpha$-naphthaleneacetic acid (NAA) and 0.075 mg $l^{-1}$ of 6-benzylaminopurine (BAP). Protoplasts were incubated in darkness at 25° C. in 8-well microchamber slides at a density of 1.25×10$^5$ cells $ml^{-1}$. Cell divisions began within 72–96 h of initiation of cultures. After 96 h, cell survival averaged 57% of the initial number of cells (n=20; range=36–84%).

After 8–10 weeks of culture, cell colonies were transferred to a callus initiation medium containing agar and incubated under continuous white fluorescent light (25 $\mu$mol $m^{-2}$ $s^{-1}$ of photons of photosynthetically active radiation) for another 8–10 weeks. Green callus tissue was then transferred to a commercial callus growth medium and incubated under similar conditions. After 8–10 weeks of further growth, callus was transferred to a commercial shoot differentiation medium and incubated similarly. Multiple shoots appeared within 2 weeks. Shoots were transferred to a root differentiation medium and cultured under the conditions described above. When roots were sufficiently developed (6–8 weeks), plants were transplanted to soil and grown in a growth chamber. It appears that guard cell protoplasts can be made to survive in culture at high percentages and that cultured guard cell protoplasts of *Nicotiana glauca* are totipotent.

It is an object of the present invention to regenerate plants.

It is another object of the present invention to regenerate plants from their guard cells.

It is another object of the present invention to provide means by which guard cells may be cultured and grown in vitro.

It is yet another object of the present invention to provide means by which guard cells may be grown and sustained practically indefinitely in vitro.

These and other objects and advantages of the present invention will be apparent from a review of the following specification and accompanying drawings.

BRIEF DESCRIPTION OF THE DRAWINGS

FIG. 1 shows recently collected guard cell protoplasts. The large organelles in the protoplasts are chloroplasts;

FIG. 2 shows the guard cell protoplasts of FIG. 1 after 96 h in culture (400×). Attention is directed to the thickening of newly-synthesized cell walls (cw), peripheral plastids (pp), cell plate (cp), and smooth morphology of guard cell chloroplasts (c);

FIG. 3 shows colonies of dividing guard cells after 3–4 weeks of growth in culture (100×);

FIG. 4 shows guard cell aggregates after 8–10 weeks of growth in liquid culture;

FIG. 5 shows the percent of cells surviving in 20 separate experiments; the line shows the average percent survival for all 20 experiments;

FIG. 6 shows the survival as a function of leaf size. The line is a least squares regression to the points ($r^2$=0.003);

FIG. 7 shows the survival as a function of distance of the leaf from the top of growing plants (insertion level). The line is a least squares regression to the points ($r^2$=0.082);

FIGS. 8–10 show photographs of the growth of callus from cell aggregates derived from cultured guard cell protoplasts of *Nicotiana glauca;*

FIG. 8 shows primary guard cell callus after 8–10 weeks of growth in light;

FIG. 9 shows secondary callus after 8–10 weeks of growth on various commercial growth media. As the cultures were initiated with roughly equal amounts of primary callus, comparison may be made of the growth on callus and root media to growth on shoot medium;

FIG. 10 show the formation of shoots from secondary callus derived from cultured guard cell protoplasts of *Nicotiana glauca;*

FIGS. 12a and 12b show chemical constituents and their concentrations present in the mediums used to culture guard cells.

DESCRIPTION OF THE PREFERRED EMBODIMENT(S).

In the present invention, guard cells are collected from the leaves of a parent plant or parent plant species. Initially, the guard cells are contaminated with other parent plant cell types. A first digestion process eliminates all other plant cells save the guard cells. A second digestion process dissolves the cell walls that encase the inner guard cell protoplast. In a highly purified form, guard cell protoplasts are made available for laboratory and/or research use, as well as the regeneration of the parent/parent species plant.

Figure 11:
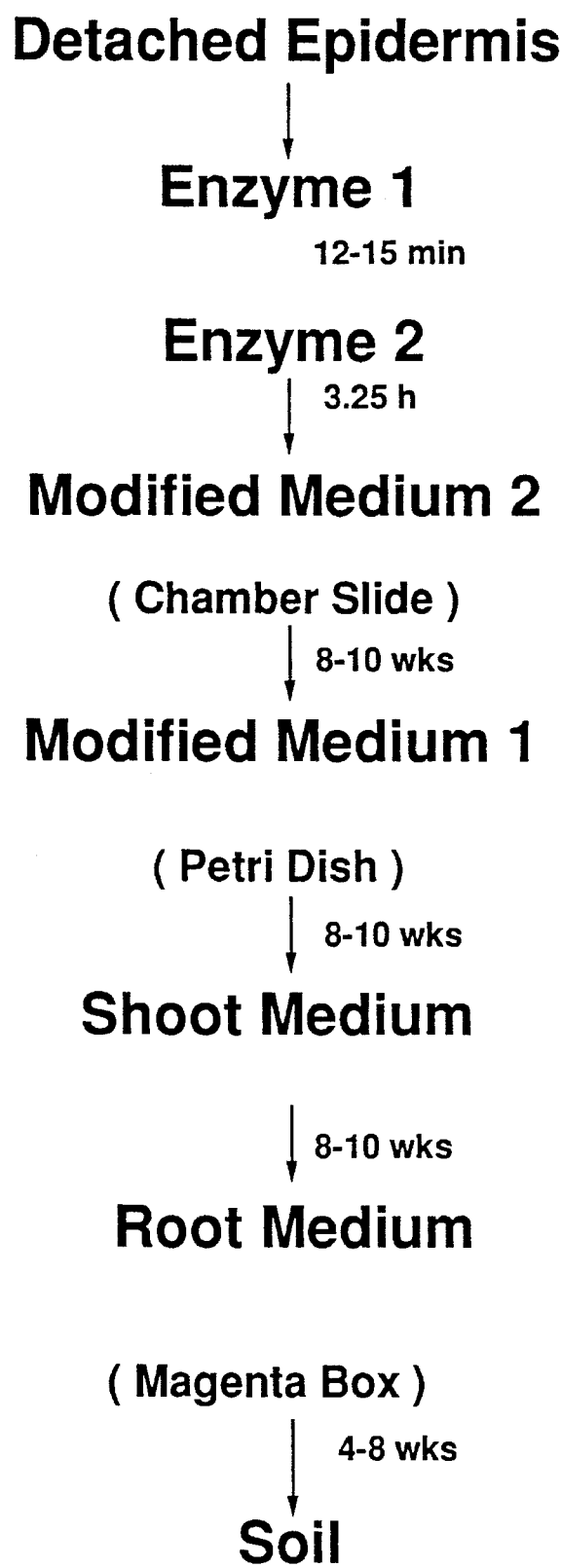
FIG. 11 shows schematically the steps involved in culturing guard cells to regenerate plants.

In order to regenerate the original donor plant, the guard cell protoplasts are stabilized and cultured to establish a viable guard cell population. Once a viable guard cell population has been established, it can be activated to form shoots and roots in the appropriate shoot-promoting or root-promoting medium, respectively. Once shoot and root growth have been fostered from a guard cell callus, the immature plant so formed may be planted in the soil in the same manner as a germinated seed from the donor plant. For the present invention, the *Nicotiana glauca* or tree tobacco plant was used and the detailed disclosure, below, reflects this. FIG. 11 shows this process schematically.

Seeds of *N. glauca* were germinated at high density on the surface of moistened, autoclaved potting soil (Supersoil, Chino, Calif., U.S.A.) in small pots (160 ml). Germinated seedlings were maintained in a growth chamber (Conviron, Pembina, N.Dak., U.S.A.). They were watered with tap water daily and every other day with Hoaglands nutrient solution. The light level at seedling height was 50–70 µmol $m^{-2}$ $s^{-1}$ of photons of photosynthetically active radiation (PAR); plants were maintained on a 12 h light/12 h dark cycle. The average temperature in the chamber during the light cycle was 25°±2° C.; the average chamber temperature during the dark cycle was 21°±2° C. Relative humidity in the chamber was 65–75%. After 4–6 weeks of growth, plants were transferred to 2 l plastic pots containing an autoclaved mixture of 60% soil/40% sand (v/v; Supersoil, Chino, Calif., U.S.A.). After another 4–6 weeks of growth, plants were culled to 2 plants per pot and allowed to grow to a height of 0.2 to 0.3 m. Plants were then transferred to 10 l plastic pots containing the same mixture of soil and sand. Plants were grown indoors on a table under high-intensity fluorescent lights (General Electric, Cleveland, Ohio, U.S.A.). The light level at the top of the canopy was 800–900 µmol $m^{-2}$ $s^{-1}$ of photons of PAR. Plants were watered 3 times daily with tap water at 6 h intervals for 4 min and every other day with Hoaglands solution. Temperatures in the room averaged 27°±2° C. during the 16 h light cycle and 23°±2° C. during the 8 h dark cycle; relative humidity was 45–65%. Plants were not used after they reached a height of 1 m.

For each experiment, flat leaves at insertion levels 21 and 22 above the cotyledons with blade lengths of 0.11 to 0.2 m and with relatively thick cuticles were harvested between 0830 and 0930 h Pacific Standard Time, prior to the onset of the light cycle, which began at 1000 h. Leaves were stored in moist paper towels in darkness until detachment of epidermis was initiated (usually 10–15 min after harvesting). All procedures were carried out with autoclaved instruments and glassware in a laminar flow cabinet. Plastic 8-well microchamber culture slides, plastic containers, and plastic pipettes were used throughout. Enzyme solutions and culture media lacking agar were sterilized by filtration through disposable 0.45 µm cellulose nitrate filters in disposable filter units (model 125-0045, Nalge Co., Rochester, N.Y., U.S.A.). Media containing agar were sterilized by autoclaving at 121° C., 15 psi for 20 min. Leaves were sprayed with 95% ethanol and then lightly buffed with tissues to remove some of the wax coating. They were then rinsed with tap water, surface sterilized by immersion for 3–5 s in 5.25% sodium hypochlorite (v/v; Clorox bleach, Oakland, Calif., U.S.A.), and rinsed 3 more times in sterile, deionized water.

Adaxial epidermis from one leaf was detached by peeling the epidermis from underlying mesophyll tissue by hand; hands were covered with a double pair of latex gloves sterilized by the same procedure as described above for leaves. Adaxial epidermis was used because its cuticle was thicker than that of the abaxial epidermis, a characteristic which made it easier to peel. Epidermis was detached under a sterile solution containing 0.5% polyvinylpyrrolidone 40 (w/v; PVP 40) and 0.05% ascorbic acid (w/v; pH 6.5) and rubbed with a cotton-tipped applicator to remove some adhering mesophyll tissue. The tissue was then cut into small strips with a razor blade and transferred to a petri dish containing the same solution.

To remove contaminating mesophyll and epidermal cells, a preliminary enzyme digestion was performed (15–18). Epidermis was transferred to 37 ml of a solution containing 0.2M sucrose, 0.7 mM $CaCl_2$, 0.4 g Cellulase Onozuka RS, 3 mg Pectolyase Y-23, 0.185 g PVP 40, and 75 mg bovine serum albumin (pH 5.5). The pH of the solution was adjusted initially to 3.4 with 0.1N HCl and allowed to stir for 7 min. The pH was then raised to 5.5 with 0.1N NaOH before filter sterilization. The tissue was incubated at 28°–29° C. for 12–15 min in an orbital shaking water bath at 175 excursions $min^{-1}$. To collect the cleaned epidermis, the flask contents were poured over a nylon net (220×220 $µm^2$ mesh). After epidermis was rinsed on the net with 100 ml of a solution containing 0.2M sucrose and 1 mM $CaCl_2$ (pH 5.5), a second digestion step was performed to release guard cell protoplasts. Epidermal strips were transferred with forceps to 25 ml of a solution containing 0.25M sucrose, 1 mM $CaCl_2$, 0.4 g Cellulase Onozuka RS, 3 mg Pectolyase Y-23, 0.125 g PVP 40, and 75 mg bovine serum albumin (pH 5.5). The pH of the solution was adjusted as described above. To release guard cell protoplasts, the suspension was incubated at 28°–29° C. for 3.25 h in a reciprocating shaking water bath at 15 excursions $min^{-1}$. At the end of the second digestion step, the suspension was filtered through a nylon net (30×30 $µm^2$ mesh) and protoplasts were collected by centrifuging the filtrate at 40 g for 6–7 min. Protoplasts were washed 3 times by centrifugation. After each centrifugation, protoplasts were resuspended in each wash medium by rolling centrifuge tubes gently between the palms of the hands. Cells were washed in the culture medium described previously, but modified as follows: 1) the concentration of $CaCl_2 \cdot H_2O$ was 85 mg $l^{-1}$; 2) the concentration of KCl was 88 mg $l^{-1}$; 3) the concentration of glycine was 1.35 g $l^{-1}$) the sucrose concentration was 0.28M; 5) mannitol was omitted from the medium; 6) the concentration of morpholino-ethanosulfonic acid (MES) buffer was 5 mM. Cells were washed in this medium first at pH 6.8, and then two more times in the same medium, but at pH 6.1. Protoplast density was estimated with a hemocytometer and the suspension was diluted with medium (pH 6.1) until the density was $1.67 \times 10^5$ cells $ml^{-1}$.

Several separate experiments aimed at identifying conditions most conducive to cell growth and survival were performed. First, three series of experiments were performed to identify optimum concentrations and ratios of the growth regulators α-naphthaleneacetic acid (NAA) and 6-benzylaminopurine (BAP). In each series, the medium described above was used except the sucrose concentration was 0.3M and the pH was 6.5. Concentrations of growth regulators were: series 1 (NAA=0.6 mg $l^{-1}$; BAP=0.1, 0.15, 0.2, or 0.3 mg $l^{-1}$); series 2 (NAA=0.4 mg $l^{-1}$; BAP=0.05, 0.06, 0.0675, 0.075, 0.085, 0.1, or 0.15 mg $l^{-1}$); series 3 (NAA=0.15, 0.225, 0.3, or 0.375 mg $l^{-1}$; BAP=0.075, mg $l^{-1}$). Under these conditions, optimum concentrations of NAA and BAP were 0.3 and 0.075 mg $l^{-1}$, respectively. To determine the optimum pH, cells were cultured in the medium described above containing 0.3 mg $l^{-1}$ NAA and 0.075 mg $l^{-1}$ BAP, but the pH of the medium was varied in 0.1 unit increments over the range of 5.5 to 6.7; the optimum pH was 6.1. To determine the optimum sucrose concentration, cells were cultured in the medium described containing 0.3 mg l$^{-1}$ NAA and 0.075 mg l$^{-1}$ BAP at pH 6.1, but sucrose concentrations were varied in increments of 0.02M over the range of 0.28 to 0.44M; the optimum sucrose concentration was 0.28M. After the optimum pH and sucrose concentrations were identified preliminarily, a final series of experiments was performed to determine whether the hormone concentration was optimal for a medium of pH 6.1 containing 0.28M sucrose. In the final series of hormone experiments the concentration of NAA was 0.15, 0.225, 0.3, or 0.375 mg l$^{-1}$; the concentration of BAP was 0.05, 0.0675, 0.075, 0.085, 0.1, or 0.150 mg l$^{-1}$. In each experiment, protoplast viability was assessed as described previously. Contamination of preparations of guard cell protoplasts with protoplasts of mesophyll cells or other epidermal cells was estimated by counting the number of those cells in a microscope field containing 1×10$^4$ guard cell protoplasts.

In all subsequent experiments liquid cultures were initiated by pipetting 0.3 ml of the cell suspension into wells of 8-well microchamber culture slides. To each chamber was added 0.1 ml of the same medium containing 1.2 mg l$^{-1}$ of NAA and 0.3 mg l$^{-1}$ of BAP, so that the final concentrations of NAA and BAP were 0.3 mg l$^{-1}$ and 0.075 mg l$^{-1}$, respectively. In some experiments, cultures were initiated in 2-well microchamber culture slides. In those experiments, 1.5 ml of the cell suspension was added to each well, followed by addition of 0.5 ml of medium containing 1.2 mg l$^{-1}$ NAA, 0.3 mg l$^{-1}$ BAP, and 20–120 g l$^{-1}$ of agarose at 40° C. (Type VII, SigTna Chemical, St. Louis, Mo, U.S.A.). Slides were incubated in sterile plastic Petri dishes (2.5 cm deep×15 cm diameter) containing moist paper towels; dishes were sealed tightly with Parafilm (American National Can Co., Greenwich, Conn., U.S.A.). Cultures were incubated at 25° C. in darkness or under red light (15–20 µmol m$^{-2}$ s$^{-1}$ of photons of PAR) on a 12 h light/12 h dark cycle. For the latter experiments, red light was provided by filtering the fluorescent light of the growth chamber through a red Plexiglas filter (100% transmittance at wavelengths between 625 and 800 nm). Survival of cells in cultures was estimated as described previously.

After 8–10 weeks of culture in microchamber slides, cultured cells were transferred to medium III of Shepard and Totten (1975) modified as follows: 1) hormone concentrations were 0.3 mg l$^{-1}$ of NAA and 0.075 mg l$^{-1}$ of BAP; 2) the sucrose concentration of was 0.23M; 3) the pH of the medium was adjusted to 6.1 and buffered with 5 mM MES; and 4) the concentration of agarose was 0.5% (w/v). Colonies were cultured on approximately 20 ml of media in tightly sealed Petri dishes (1.5 cm deep×10 cm diameter) incubated at 25° C. in darkness or under continuous white fluorescent light (21–27 µmol m$^{-2}$ s$^{-1}$ of photons of PAR). After 8–10 weeks, green callus tissue from light-grown cultures was transferred to one of three commercial media (all from Carolina Biological Supply, Gladstone, Oreg., U.S.A.): a medium used to support the growth of callus of N. tabacum, a medium used to initiate shoot differentiation from callus of N. tabacum, or a medium used to initiate root differentiation from callus of N. tabacum. All three media contained the salts described by Murashige and Skoog (1962) and 100 mg l$^{-1}$ of i-inositol, 0.5 mg l$^{-1}$ of nicotinic acid, 0.5 mg l$^{-1}$ of pyridoxine HCl, 0.4 mg l$^{-1}$ of thiamine HCl, 2 mg l$^{-1}$ of glycine, 1 g l$^{-1}$ of casein hydrolysate, and 0.8 g l$^{-1}$ of agar. The shoot medium contained 1 mg l$^{-1}$ of kinetin; the callus medium contained 2 mg l$^{-1}$ of indole-3-acetic acid (IAA) and 0.2 mg l$^{-1}$ of kinetin; the root medium contained 3 mg l$^{-1}$ of IAA. Cultures were incubated at 25° C. under continuous white fluorescent light (14–23 µmol m$^{-2}$ s$^{-1}$ of photons of PAR). After 8–10 weeks of growth on callus medium, the tissue was transferred to shoot differentiation medium. When shoots were 0.5 to 1 cm in height they were transferred to Magenta vessels (Sigma Chemical Co., St. Louis, Mo., U.S.A.) containing 75 ml of 0.5× salts and organics of medium III of Shepard and Totten (1975), 0.025M sucrose, 0.6% phytagar, and no growth regulators. Shoots were cultured at 25° C. under continuous white fluorescent light (30 µmol m$^{-2}$ s$^{-1}$ of photons of PAR). When roots were sufficiently developed (6–8 weeks), plants were transplanted to small pots and grown under the conditions described above for seedlings.

Figure 1:
FIGS. 1–4 are photographic, top plan views of the growth of guard cell protoplasts isolated from adaxial epidermis of *Nicotiana glauca* in liquid culture as described herein using differential interference contrast optics (200×; bar= 30 $\mu$m)
Figure 2:
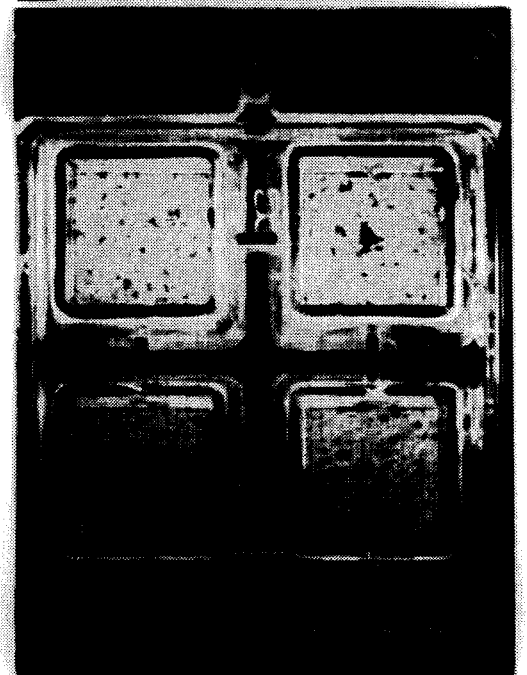
Figure 5:
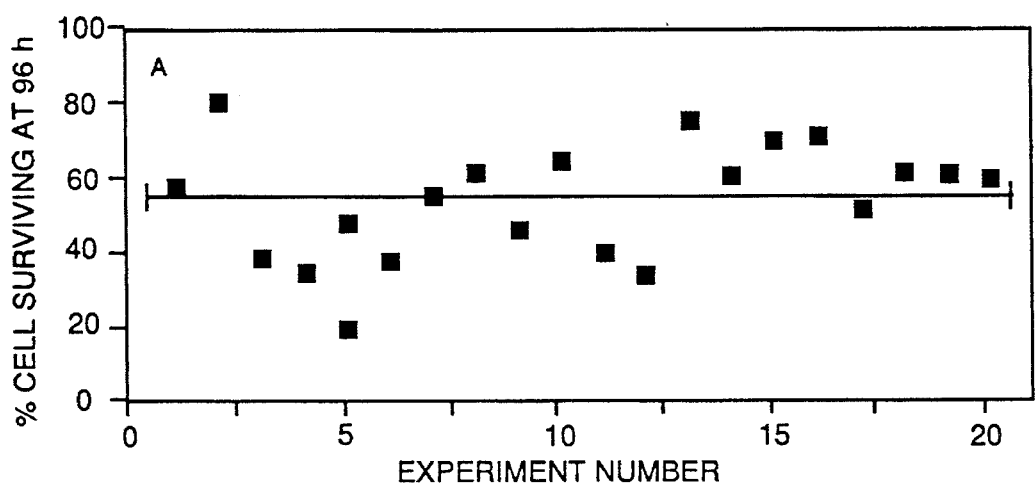
FIGS. 5–7 are graphs showing the percent of guard cell protoplasts of *Nicotiana glauca* surviving 96 h in liquid cultures. In each experiment, cells were cultured under optimal conditions as described herein (pH 6.1, sucrose= 0.28M, NAA= 0.3 mg $l^{-1}$, BAP=0.075 mg $l^{-1}$)
Figure 6:
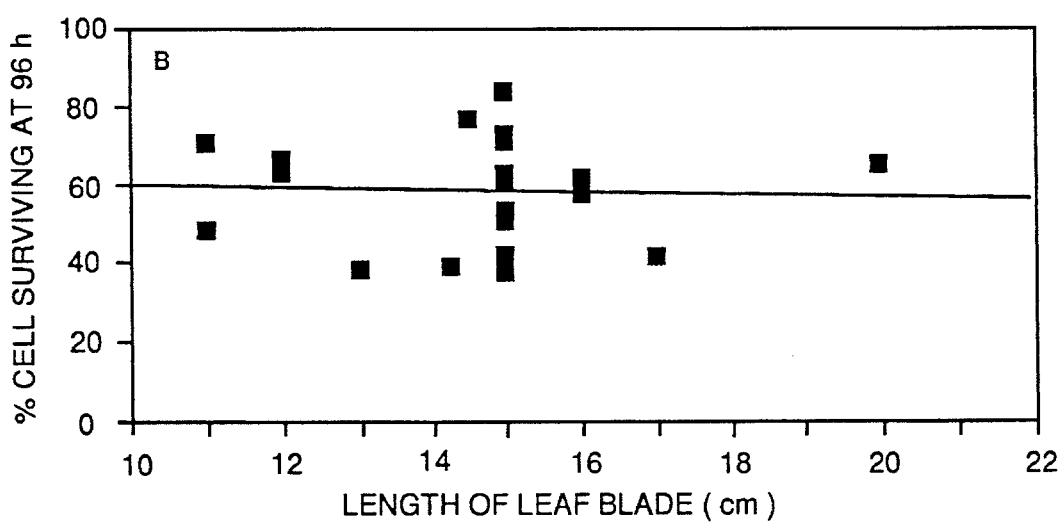
Figure 7:
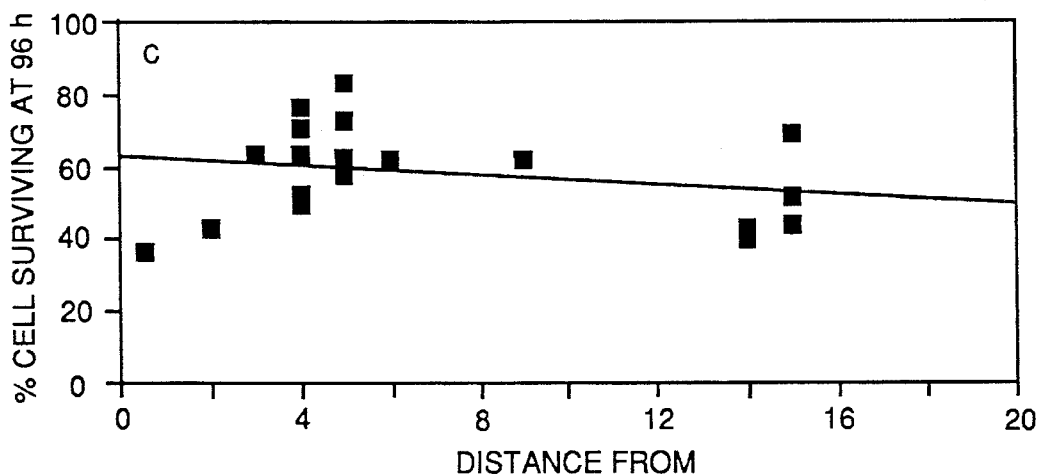

Guard cell protoplasts were easily distinguished by their morphology from protoplasts of other epidermal cells, from protoplasts of mesophyll cells, and from subprotoplasts of both cells types; all of these cell types have been described previously. Contamination of preparations of guard cell protoplasts with other cell types was <0.01% (FIG. 1). Within 48–96 h in culture, protoplasts had grown and regenerated cell walls and cell divisions had begun (FIG. 2). During the first week of culture, the large, bumpy morphology characteristic of guard cell plastids (FIG. 1) changed, and plastids gradually became smaller and more smooth (FIG. 2), probably due to loss of starch. Some plastids appeared at the periphery of growing cells just beneath the plasma membrane (FIG. 2). The percentage of cells surviving to 96 h in culture averaged 57% (n=20; range 36–84%; FIG. 5). There was no correlation between the percentage of cells surviving to 96 h and either the length of the leaf blade (FIG. 6) or the distance of the leaf from the top of the plant (insertion level; FIG. 7). In liquid media, differences in sucrose concentrations ranging from 0.28 to 0.34M or pH values ranging from 6.1 to 6.7 had little effect on cell survival to 96 h; cell survival was lower at pH values between 5.5 and 5.9 (not shown). Optimal concentrations of NAA and BAP were determined to be 0.3 mg l$^{-1}$ and 0.075 mg l$^{-1}$, respectively (not shown). Even at low hormone levels, survival was poor when cultures were incubated under continuous white light. When cells were incubated under similar fluences of continuous red light, protoplasts grew rapidly and reached the division state after only 48 h, but cell divisions ceased after 1–2 weeks in culture. In one red light experiment in which cells were suspended in a modified medium containing 30 g l$^{-1}$ of agarose, 0.3 mg l$^{-1}$ NAA, and no BAP, cells were observed to divide after one week of culture (not shown).

Figure 3:
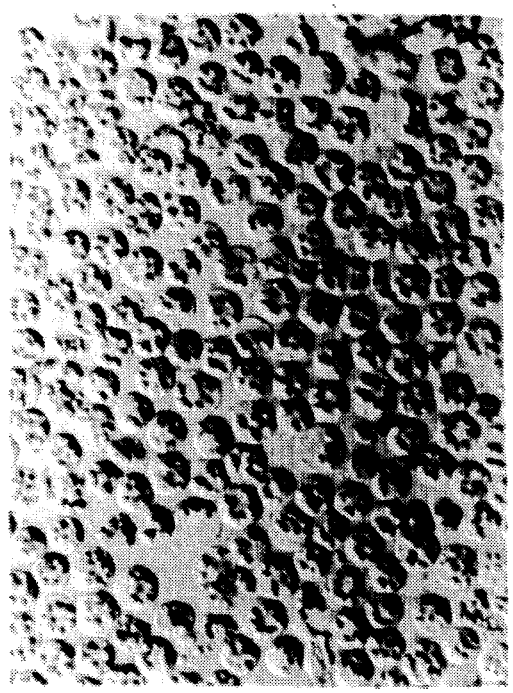
Figure 4:
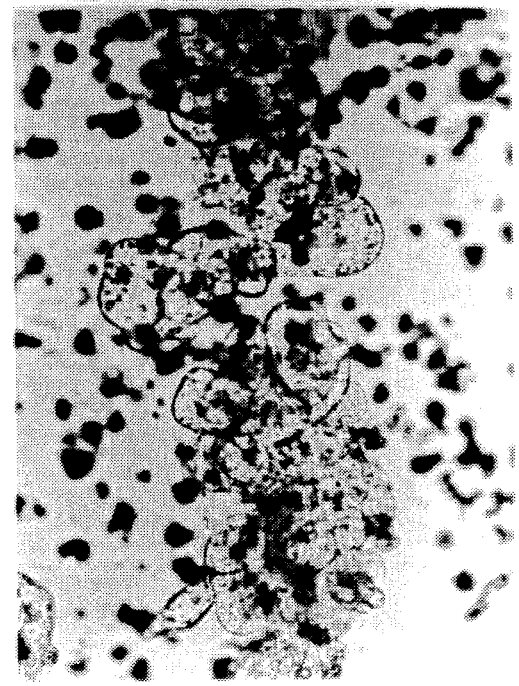

Small colonies of cells were visible after 1 week of culture (not shown) and larger colonies within 3–4 weeks (FIG. 3). In liquid cultures, colonies aggregated to fill the bottoms of wells of culture slides in 8–10 weeks (FIG. 4). Over the same period, colonies derived from protoplasts embedded in agar grew more slowly and were smaller than those grown in liquid media, but embedded colonies grew at relatively high densities (not shown). Upon transfer to callus initiation media, colonies grew rapidly in light, producing green callus in 8–10 weeks (FIG. 8). Colonies incubated under similar conditions in darkness also produced callus, but the callus grew more slowly and did not turn green (not shown). Occasionally, adventitious roots appeared on callus tissue incubated in tightly sealed containers under continuous fluorescent light (not shown). When primary, green callus was transferred to a commercial callus growth medium or to a commercial root differentiation medium, callus turned a pale brown and grew slowly (FIG. 9). Callus remained green and grew rapidly on a commercial shoot differentiation medium (FIG. 9). Regardless of whether primary callus or secondary callus grown on a commercial callus medium was used, shoots were produced within 2–4 weeks of transfer to the commercial shoot differentiation medium (FIG. 10). When shoots were transferred to a rooting medium, roots appeared within 6–8 weeks (not shown). After they were transplanted to soil, plants grew vigorously in the growth chamber (not shown). Guard cells of regenerated plants contained the same average number of chloroplasts per cell (mean=10; S.D.=1.1; n=100) as those of the parental plants used to prepare the original isolates (mean=11, S.D.=1.1; n=100).

When guard cell protoplasts of *N. glauca* are cultured by the procedure described, the resulting callus is totipotent. Furthermore, when culture conditions are adjusted appropriately, a high percentage of guard cell protoplasts of *N. glauca* survive in culture. Because studies of guard cell biochemistry and metabolism require preparations of guard cell protoplasts that are virtually free of contamination with other cell types, good methods have been developed for preparing protoplast isolates that are highly enriched in guard cell protoplasts. Both in a previous study and in this study, levels of contamination with mesophyll cell protoplasts and protoplasts of other epidermal cells were low (total<0.01%). Because only $5 \times 10^4$ protoplasts were incubated in each well of a chamber slide, the number of contaminating epidermal and mesophyll protoplasts per well was no more than 5 per well on average. Attempts to culture mesophyll protoplasts of *N. glauca* isolated and cultured by this same method failed, probably because the concentrations and/or ratios of plant growth regulators that were optimal for survival of guard cell protoplasts were not those that were optimal for growth and survival of mesophyll cell protoplasts (data not shown). Similarly, observation of individual contaminating epidermal cells revealed that they did not survive under these same conditions. Because the callus derived from liquid cultures of guard cell protoplasts was from a single cell type, it is believed that this is an unequivocal demonstration of the totipotency of callus derived from cultured guard cell protoplasts.

The average percentage of cells surviving 96 h in culture was more than 6 times that reported in the previous study. Indeed, whereas the low percentage of cells surviving 96 h in the previous study (<10%) enabled us to estimate division of the few surviving cells for up to 12 days, in these studies, overlap of colonies formed by dividing cells prevented us from estimating survival percentages beyond 96 h. Various modifications to the methods described in the previous study account for the increased percentage (57%) of guard cell protoplasts that survived to 96 h in this current study: 1) Plants were grown under fluorescent light indoors and only young, flat leaves with relatively thick cuticles were used. While there was no correlation between leaf size or insertion level for plants <1 m in height, there did appear to be a lower survival of guard cell protoplasts from older plants that were >1 m in height. Speculation may be made that the leaves used in these experiments had a lower content of flavonoids and phenolic compounds than those used in previous experiments, improving the viability of the freshly isolated cells. 2) Leaves were harvested in darkness just prior to the onset of the daily light period. Thus, the osmotic potentials of guard cell protoplasts isolated from leaves in which stomata were closed initially were presumably less negative and more uniform than those of the guard cell protoplasts isolated from leaves with open stomata that, in previous experiments, were harvested during the light period. 3) The addition of PVP 40 and ascorbate to the solution in which epidermis was detached from the leaf appeared to enhance cell survival, probably by inhibiting damage by phenolic compounds released from the tissue. 4) Throughout the isolation procedure, protoplasts were resuspended after centrifugation by rolling centrifuge tubes gently between the palms of the hands instead of by more destructive vortex mixing. 5) All containers in which cells were isolated and cultured and all pipettes were made of plastic; glass pipettes and vessels with rougher surfaces appeared to decrease both yield and survival. 6) Sucrose was used instead of mannitol as the primary osmoticum, both in the isolation procedures and in culture media. The sucrose concentration required to stabilize guard cell protoplasts osmotically was one half the combined concentrations of mannitol and sucrose required to stabilize the protoplasts in previous experiments. It is not clear why sucrose could be used at lower concentrations, but it is speculated that energy provided by sucrose catabolism may have enhanced the capacity of guard cell protoplasts to osmoregulate. 7) Potassium ions accumulate in guard cells during stomatal opening, while calcium ions may be an important part of the mechanism of stomatal closure. It seems reasonable that elevating the levels of these important ions to levels found in apoplastic water of *N. glauca* might enhance survival. Thus, the concentrations of potassium ions and calcium ions were elevated in the culture medium to levels reported for expressed xylem water of this species. 8) The concentrations of NAA and BAP were reduced to 0.3 mg $l^{-1}$ and 0.075 mg $l^{-1}$, respectively. These concentrations were one fourth those used in previous experiments and were considerably lower than those used to culture mesophyll protoplasts of this genus. Tests were made of a wide range of concentrations and ratios of these two hormones, and these were found to be optimal. Speculation may be made that guard cell protoplasts may require lower concentrations of growth regulators either because they have smaller surface-to-volume ratios than mesophyll cell protoplasts and/or because they possess higher densities of receptors for plant growth regulators than do mesophyll cell protoplasts. 9) Because cell survival was poor when cultures were illuminated with white light, cultures were incubated in darkness instead of with white light as described previously. White light contains a significant blue light component which is known to cause guard cells to swell. Because guard cell protoplasts were devoid of a cell wall at the time cultures were initiated, it is possible that white light caused the protoplasts to swell and burst before they could regenerate the cell walls necessary for maintenance of normal turgor relations. Survival was improved under red light, and results of one red light experiment in which no cytokinin was added to the medium indicated that exogenous cytokinin may not be an absolute requirement for division of cultured guard cell protoplasts. As in previous experiments, survival did not seem to be a function of cell density.

In other species, the number of chloroplasts per guard cell is directly proportional to the ploidy of the plant. The observation that guard cells of regenerated plants had the same number of chloroplasts as those of parental plants suggests that the ploidy of cultured guard cells did not change. The totipotency of guard-cell derived callus indicates that the culture procedures employed did not grossly alter the functionality of the nuclear, mitochondrial, or plastid genomes of these cells. Because these data indicate that cultured guard cells possess genomic integrity, it is anticipated that observed differences in the cellular physiology of freshly isolated guard cell protoplasts and cultured cells should be due mainly to the culture environment and not due to irreversible alterations of the genome brought on by culture conditions. Thus, cultured guard cell protoplasts should be useful for a number of comparative studies of changes in cell physiology initiated by alterations to the environment surrounding the cultured cells.

In an alternative embodiment of the present invention, significant strides can be made to advantageously and usefully modify the transpirational and photosynthetic characteristics of a plant. Consequently, certain growth characteristics and biological operations of the plant may be modified as well. As gas exchange for a plant occurs via the stoma, and as the stoma are regulated by the guard cells, modification of the guard cells alters the behavior of the stoma.

The purified guard cell protoplast culture described herein provides an excellent source of raw genetic material for refinement. When the gene or genes for controlling guard cell behavior for one species of plant are isolated, they can be transferred to guard cells of another species. With this transfer, the behavior of the guard cells of the second species would then resemble, if not become identical to, the guard cells of the first species. As the guard cells of a plant can regenerated the plant entirely, culturing the modified guard cells of the second plant species should yield a new variety of second plant species having enhanced guard cell and stoma behavior.

One example of such guard cell modification would be where a wheat or corn plant has its guard cells modified so that the plant retains more water. As guard cells of drought tolerant chaparral plants such as laurel sumac may provide excellent guard cell genes for plant water conservation, the genetic introduction of laurel sumac guard cell behavior into wheat or corn may allow such food plants to survive in regions where water is scarce or needs to be conserved.

While the present invention has been described with regards to particular embodiments, it is recognized that additional variations of the present invention may be devised without departing from the inventive concept.

What I claim is:

1. A method of regenerating Nicotiana glauca plants, the steps comprising:
    isolating guard cell protoplasts;
    growing said guard cell protoplasts to establish a viable callus cell population;
    promoting shoot and root growth in said callus cell population to form an immature plant; and
    planting said immature plant.

2. The method of regenerating plants of claim 1, wherein the step of isolating guard cell protoplasts comprising:
    collecting a leaf sample;
    separating an epidermal layer from said leaf sample;
    subjecting said epidermal layer to a digestion process;
    collecting a residue remaining from said digestion process, said residue having a high concentration of said guard cell protoplasts.

3. The method of regenerating plants of claim 2, wherein the step of separating an epidermal layer from said leaf sample further comprising:
    separating said epidermal layer under a sterile solution comprising approximately:
    0.5% polyvinylpyrrolidone 40 (PVP 40); and
    0.5% ascorbic acid;
    said sterile solution of pH approximately 6.5.

4. The method of regenerating plants of claim 2, wherein said digestion process comprising:
    cleaning said epidermal layer to provide a cleaned epidermis; and
    releasing said guard cell protoplasts.

5. The method of regenerating plants of claim 4, wherein the step of cleaning said epidermal layer comprising:
    placing said epidermal layer in a first solution having a pH and comprising approximately:
    0.2M sucrose;
    0.7 mM calcium chloride;
    10.81 g/l Cellulase Onozuka RS;
    0.081 g/l Pectolyase Y-23;
    5 g/l polyvinylpyrrolidone 40 (PVP 40); and
    2.027 g/l bovine serum albumin;
    initially adjusting said pH of said first solution to approximately 3.4;
    stirring said first solution for approximately 7 minutes;
    raising said pH of said first solution to approximately 5.5; and
    incubating said epidermal layer at 28°–29° C. for approximately 12–15 minutes in an orbital shaking bath at approximately 175 excursions per minute to form a cleaned epidermis.

6. The method of regenerating plants of claim 4, wherein said digestion process further comprising:
    collecting said cleaned epidermis; and
    rinsing said cleaned epidermis with a solution comprising 0.2M sucrose and 1 mM calcium chloride at an approximate pH of 5.5.

7. The method of regenerating plants of claim 4, wherein the step of releasing said guard cell protoplasts comprising:
    rinsing said cleaned epidermis;
    placing said cleaned epidermis in a second solution having a pH and comprising approximately:
    0.25M sucrose;
    1 mM calcium chloride;
    16 g/l Cellulase Onozuka RS;
    0.12 g/l Pectolyase Y-23;
    5 g/l polyvinylpyrrolidone 40 (PVP 40); and
    3 g/l bovine serum albumin;
    initially adjusting said pH of said second solution to approximately 3.4;
    stirring said second solution for approximately 7 minutes;
    raising said pH of said second solution to approximately 5.5; and
    incubating said cleaned epidermis at approximately 28°–29° C. for approximately 3.25 hours in a reciprocating shaking bath at approximately 15 excursions per minute to form a suspension.

8. The method of regenerating plants of claim 2, wherein the step of collecting a residue remaining from said digestion process comprising:
    separating suspended material in said suspension from a filtrate having said guard cell protoplasts; and
    centrifuging said filtrate to form a centrifugate.

9. The method of regenerating plants of claim 8, wherein the step of collecting a residue remaining from said digestion process further comprising:
    pouring off a liquid portion of said centrifugate, leaving a guard cell protoplast mass;
    adding a wash medium to said guard cell protoplast mass;
    gently suspending guard cell protoplasts of said guard cell protoplast mass in said wash medium; and
    centrifuging said wash medium to form another centrifugate.

10. The method of regenerating plants of claim 9, wherein the step of adding a wash medium further comprising adding a wash medium comprising approximately:

0.085 g/l hydrous calcium chloride (CaCl$_2\cdot$H$_2$O);
0.088 g/l potassium chloride;
1.35 g/l glycine;
0.28M sucrose; and
5 mM of morpholino-ethanosulfonic acid (MES).

11. The method of regenerating plants of claim 10, wherein the steps of claim 9 are repeated, first with said wash medium of pH approximately 6.8, then with two of said wash mediums of pH approximately 6.1.

12. The method of regenerating plants of claim 1, wherein the step of growing said guard cell protoplasts to establish a viable callus cell population further comprising growing said guard cell protoplasts in a first medium comprising approximately:
   0.28M sucrose;
   0.3 mg/l α-naphthaleneacetic acid (NAA); and
   0.075 mg/l 6-benzylaminopurine (BAP);
   said first medium having an approximate pH of 6.1.

13. The method of regenerating plants of claim 12, wherein said medium further comprising:
   approximately 5–30 g/l of agarose.

14. The method of regenerating plants of claim 12, wherein the step of growing said guard cell protoplasts to callus cells further comprising growing said guard cell protoplasts in darkness to form callus cells.

15. The method of regenerating plants of claim 12, wherein the step of growing said guard cell protoplasts to callus cells further comprising:
   illuminating said guard cell protoplasts with red light of wavelengths approximately between 625 and 800 nm and of fluence approximately 15–20 μmol m$^{-2}$ s$^{-1}$ of photons of photosynthetically active radiation (PAR) to form callus cells.

16. The method of regenerating plants of claim 15, wherein said red light is cycled on an approximately 12 hour light/12 hour dark cycle.

17. The method of regenerating plants of claim 15, further comprising the steps of:
   transferring grown callus cells of said viable callus cell population to a second medium comprising approximately:
      0.3 mg/l α-naphthaleneacetic acid (NAA);
      0.075 mg/l 6-benzylaminopurine (BAP);
      0.23M sucrose;
      5 mM morpholino-ethanosulfonic acid (MES); and
      0.5% agarose;
   said second medium having an approximate pH of 6.1.

18. The method of regenerating plants of claim 17, further comprising the step of incubating said transferred callus cells in darkness.

19. The method of regenerating plants of claim 17, further comprising the step of incubating said transferred callus cells in tightly sealed Petri dishes.

20. The method of regenerating plants of claim 17, further comprising the step of illuminating said second-medium callus cells with continuous white light of approximately 21–27 μmol m$^{-2}$ s$^{-1}$ of photons of photosynthetically active radiation (PAR) to establish a viable callus cell population.

21. The method of regenerating plants of claim 1, wherein the step of promoting shoot and root growth in said callus cell population comprising:
   transferring said viable callus cell population to a callus medium comprising approximately:
      0.2 mg/l indole-3-acetic acid (IAA); and
      0.2 mg/l kinetin to further establish guard cell callus;
   transferring said guard cell callus to a shoot medium comprising approximately:
      1 mg/l kinetin to establish shooted guard cell callus; and
   transferring said shooted guard cell callus to a root medium comprising approximately:
      3 mg/l indole-3-acetic acid (IAA) to form an immature plant.

22. The method of regenerating plants of claim 21, where each of said callus, shoot, and root mediums further comprise approximately:
   100 mg/l i-inositol;
   0.5 mg/l nicotinic acid;
   0.5 mg/l pyridoxine HCL;
   0.4 mg/l thiamine HCL;
   2 mg/l glycine;
   1 g/l casein hydrolysate; and
   0.8 g/l agar.

23. The method of regenerating plants of claim 22, further comprising the step of illuminating said shooted guard cell callus with continuous white light of approximately 30 μmol m$^{-2}$ s$^{-1}$ of photons of photosynthetically active radiation (PAR).

24. The method of regenerating plants of claim 22, wherein said root medium further comprising:
   0,025 sucrose; and
   0.6% phytagar.

25. A method of regenerating *Nicotiana glauca* plants, the steps comprising:
   collecting a leaf sample;
   separating an epidermal layer from said leaf sample under a sterile solution comprising approximately 0.5 % polyvinylpyrrolidone 40 (PVP 40) and 0.5 % ascorbic acid of pH approximately 6.5;
   placing said epidermal layer in a first solution having a pH and comprising approximately:
      0.2M sucrose;
      0.7 mM calcium chloride;
      10.81 g/l Cellulase Onozuka RS;
      0.081 g/l Pectolyase Y-23;
      5 g/l polyvinylpyrrolidone 40 (PVP 40); and
      2.027 g/l bovine serum albumin;
   initially adjusting said pH of said first solution to approximately 3.4;
   stirring said first solution for approximately 7 minutes;
   raising said pH of said first solution to approximately 5.5;
   incubating said epidermal layer at 28°–29° C. for approximately 12–15 minutes in an orbital shaking bath at approximately 175 excursions per minute to form a cleaned epidermis;
   collecting said cleaned epidermis;
   rinsing said cleaned epidermis with a solution comprising 0.2M sucrose and 1 mM calcium chloride at an approximate pH of 5.5;
   placing said cleaned epidermis in a second solution having a pH and comprising approximately:
      0.25M sucrose;
      1 mM calcium chloride;
      16 g/l Cellulase Onozuka RS;
      0.12 g/l Pectolyase Y-23;
      5 g/l polyvinylpyrrolidone 40 (PVP 40); and
      3 g/l bovine serum albumin;
   initially adjusting said pH of said second solution to approximately 3.4;
   stirring said second solution for approximately 7 minutes;
   raising said pH of said second solution to approximately 5.5 to form digested epidermis;

incubating said digested epidermis at approximately 28°–29° C. for approximately 3.25 hours in a reciprocating shaking bath at approximately 15 excursions per minute to form a suspension;

separating suspended material in said suspension from a flitrate having said guard cell protoplasts;

centrifuging said filtrate to form a centrifugate;

pouring off a liquid portion of said centrifugate, leaving a guard cell protoplast mass;

adding a wash medium to said guard cell protoplast mass, comprising:
    0.085 gl hydrous calcium chloride ($CaCl_2 \cdot H_2O$);
    0.088 g/l potassium chloride;
    1.35 g/l glycine;
    0.28M sucrose; and
    5 mM of morpholino-ethanosulfonic acid (MES);

gently suspending guard cell protoplasts of said guard cell protoplast mass in said wash medium;

centrifuging said wash medium to form another centrifugate;

repeating said pouring off step, said adding wash medium step, said gentle suspension step, and said centrifugation step, first with a wash medium of pH approximately 6.8, then with two additional wash mediums of pH approximately 6.1;

growing said guard cell protoplasts in a first medium comprising approximately:
    0.28M sucrose;
    0.3 mg/l α-naphthaleneacetic acid (NAA); and
    0.075 mg/l 6-benzylaminopurine (BAP);

said first medium having an approximate pH of 6.1;

illuminating said guard cell protoplasts with red light of wavelengths approximately between 625 and 800 nm and of fluence approximately 15–20 µmol $m^{-2}$ $s^{-1}$ of photons of photosynthetically active radiation (PAR) wherein said red light is cycled on an approximately 12 hour light/12 hour dark cycle;

transferring said grown guard cell protoplasts to a second medium comprising approximately:

0.3 mg/l α-naphthaleneacetic acid (NAA);
    0.075 mg/l 6-benzylaminopurine (BAP);
    0.23M sucrose;
    5 mM morpholino-ethanosulfonic acid (MES); and
    0.5 % agarose;

said second medium having an approximate pH of 6.1;

illuminating said second-medium guard cell protoplasts in tightly sealed Petri dishes with continuous white light of approximately 21–27 µmol $m^{-2}$ $s^{-1}$ of photons of photosynthetically active radiation (PAR) to establish a viable callus cell population;

transferring said viable callus cell population to a callus medium comprising approximately:
    0.2 m/l indole-3-acetic acid (IAA); and
    0.2 mg/l kinetin to further establish guard cell callus;

transferring said guard cell callus to a shoot medium comprising approximately:
    1 mg/l kinetin to establish shooted guard cell callus;

illuminating said shooted guard cell callus with continuous white light of approximately 30/µmol $m^{-2}$ $s^{-1}$ of photons of photosynthetically active radiation (PAR);

transferring said shooted guard cell callus to a root medium comprising approximately:

3 mg/l indole-3-acetic acid (IAA) to form an immature plant; and planting said immature plant.

26. The method of regenerating plants of claim 25, wherein each of said callus, shoot, and root mediums further comprise approximately:
    100 mg/l i-inositol;
    0.5 mg/l nicotinic acid;
    0.5 mg/l pyridoxine HCL;
    0.4 mg/l thiamine HCL;
    2 mg/l glycine;
    1 g/l casein hydrolysate; and
    0.8 gl agar.

* * * * *